US00PP29269P3

(12) United States Plant Patent
Snijder

(10) Patent No.: US PP29,269 P3
(45) Date of Patent: May 1, 2018

(54) POINSETTIA PLANT NAMED 'EURZ0003'

(50) Latin Name: *Euphorbia pulcherrima*
Varietal Denomination: EURZ0003

(71) Applicant: SYNGENTA PARTICIPATIONS AG, Basel (CH)

(72) Inventor: Ronald Snijder, Andijk (NL)

(73) Assignee: Syngenta Participations AG, Basel (CH)

( * ) Notice: Subject to any disclaimer, the term of this patent is extended or adjusted under 35 U.S.C. 154(b) by 83 days.

(21) Appl. No.: 14/998,953

(22) Filed: Mar. 9, 2016

(65) Prior Publication Data

US 2017/0265351 P1 Sep. 14, 2017

(51) Int. Cl.
*A01H 5/12* (2018.01)

(52) U.S. Cl.
USPC ..... Plt./306

(58) Field of Classification Search
USPC ..... Plt./306
See application file for complete search history.

(56) References Cited

PUBLICATIONS

UPOV hit on poinsettia plant named 'EURZ0003', QZ PBR 2015/3056, application date Dec. 17, 2015.*

* cited by examiner

*Primary Examiner* — Anne Marie Grunberg
(74) *Attorney, Agent, or Firm* — Dale Skalla

(57) ABSTRACT

A new Poinsettia plant named 'EURZ0003' particularly distinguished by the distinct dark pink bract color, dark green foliage, and medium to strong vigor with good branching and strong stems.

1 Drawing Sheet

Latin name of the genus and species of the plant claimed: *Euphorbia pulcherrima.*

Varietal denomination: 'EURZ0003'.

BACKGROUND OF THE NEW PLANT

The present invention comprises a new Poinsettia, botanically known as *Euphorbia pulcherrima*, and hereinafter referred to by the variety name 'EURZ0003'.

'EURZ0003' is a product of a naturally occurring mutation. The new cultivar has dark pink bract color, medium size inflorescences with bracts a little upright directed, dark green foliage, and strong vigor with good branching, 'EURZ0003' originates from naturally occurring mutation discovered among greenhouse plants of the parent variety 'Fismars 339' (U.S. Plant Pat. No. 21,054) in fall to winter 2009. The first asexual propagation was made by taking shoot tip cuttings in Enkhuizen, Netherlands.

A greenhouse crop was developed from the first mutated plant and evaluated for its different bract color. These plants were multiplied separately and examined during next fall-winter flowering for uniformity and stability of the new combination of characteristics.

BRIEF SUMMARY OF INVENTION

Horticultural examination of plants grown from cuttings of the plant initiated in April 2010, and continuing thereafter, has demonstrated that the combination of characteristics as herein disclosed for 'EURZ0003' are firmly fixed and are retained through successive generations of asexual reproduction.

'EURZ0003' has not been observed under all possible environmental conditions. The phenotype may vary significantly with variations in environment such as temperature, light intensity and day length.

A Plant Breeder's Right for this cultivar was applied for in the European Union on Dec. 17, 2015 and assigned No. 2015/3056. 'EURZ0003' has not been made publicly available more than one year prior to the filing of this application.

The following traits have been repeatedly observed and are determined to be basic characteristics of the new variety. The combination of these characteristics distinguishes this Poinsettia as a new and distinct variety.

BRIEF DESCRIPTION OF THE PHOTOGRAPHS

The accompanying photographic drawings show typical flower and foliage characteristics of 'EURZ0003' with colors being as true as possible with an illustration of this type. The photographic drawings show flowering potted plants of the new variety.

Figure 1:
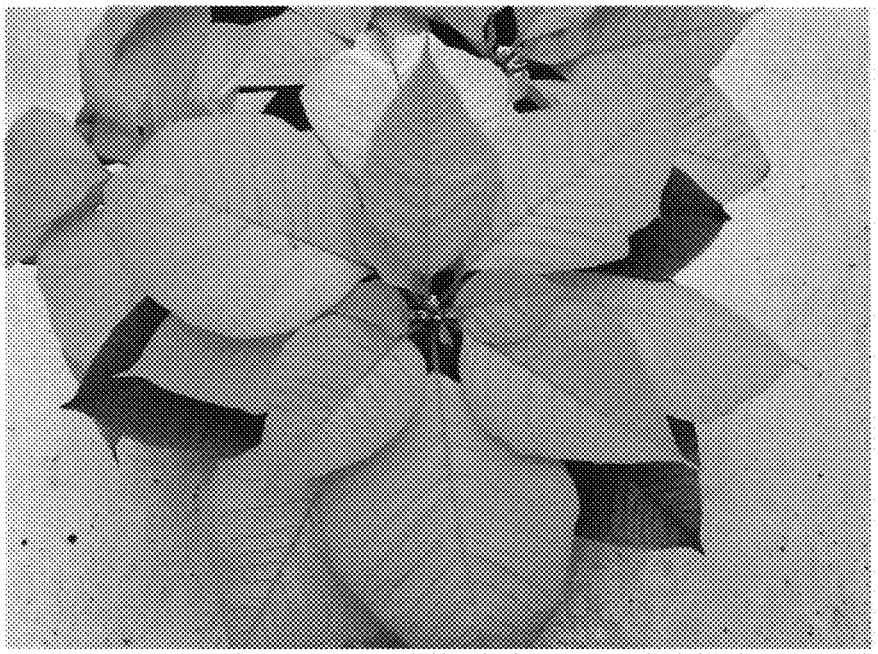
Figure 2:
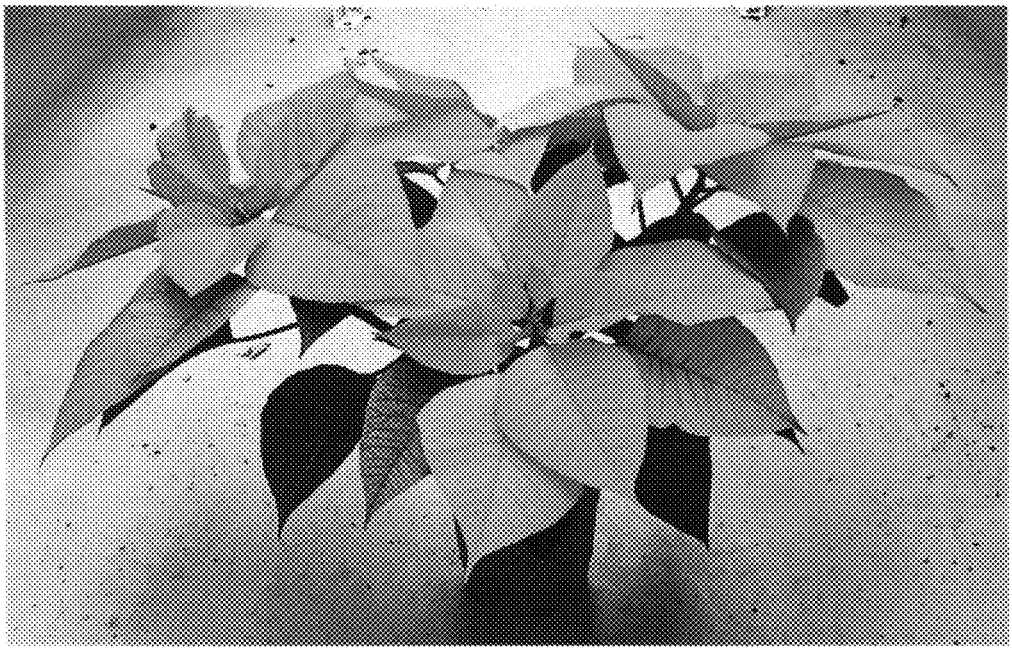

FIG. 1, taken on Nov. 27, 2015 shows a view of the bracts from the top of plant, on a plant about 21 weeks old;

FIG. 2, taken on Nov. 27, 2015, shows a side view of the same plant.

DETAILED BOTANICAL DESCRIPTION

The measurements were taken in Enkhuizen, the Netherlands in end November 2015 on 21 week old plants growing in a greenhouse. Culture of these plants had started in late June 2015 with planting rooted cuttings in 19 cm pots and terminal pinching about 2 weeks later. The plants were grown under natural day light in the fall (no black cloth to initiate earlier flowering) and at the moderately warm temperature of 18° C. for the bench heating. No use of PGR.

Color references are made to The Royal Horticultural Society Colour Chart (R.H.S.) 2001.

TABLE 1

DIFFERENCES BETWEEN THE NEW VARIETY 'EURZ0003' AND SIMILAR VARIETIES

| | 'EURZ0003' | 'Fismars 339' | 'Fismars Pink' |
|---|---|---|---|
| Bract color: | Dark pink (RHS 51A) | Red (RHS 185A) | (Pink) RHS 55A |

Plant:

*Form, growth and habit.*—Shrub, with the branches slanting upright, good branching.

*Plant height (inflorescence included).*—25-30 cm.

*Plant width.*—40-50 cm.

Roots:

*Number of days to initiate roots.*—18-20 days at about 24 degrees C.

*Number of days to produce a rooted cutting.*—24-26 days at 24 degrees C.

*Type.*—Fine, fibrous, free branching.

*Color.*—RHS N155B but whiter.

Foliage:

*Arrangement.*—Alternate, 6-11 leaves per branch.

*Immature, leaf color, upper surface.*—Approximately RHS 147A.

*Lower surface.*—RHS 137B.

*Mature, leaf color, upper surface.*—RHS 147A.

*Lower surface.*—RHS 137B.

*Length.*—11-12 cm.

*Width.*—7.5-8.5 cm.

*Shape.*—Ovate, with almost no lobes.

*Base shape.*—Truncate to obtuse.

*Apex shape.*—Acuminate.

*Margin.*—Entire; lobes, when present mostly rounded.

*Aspect.*—Leaf blades are horizontally or slightly downwards directed.

*Texture, upper surface.*—Smooth.

*Lower surface.*—Smooth, apart from the protruding veins.

*Color of veins, upper surface.*—RHS 144B and very light RHS 183D for the central vein at the base, turning to RHS 144B towards the leaf tip.

*Color of veins, lower surface.*—RHS 147C, central vein RHS 183D fading towards the leaf tip.

*Petiole color, upper surface.*—RHS 187B-C.

*Lower surface.*—RHS 184B.

*Length.*—4.5 cm.

*Diameter.*—0.35 cm.

*Aspect.*—Horizontally to slightly upward directed.

*Texture.*—Glabrous.

Stem:

*Quantity of main branches per plant.*—About 4 to 7.

*Color of stem.*—Mix of RHS 183D and RHS 147B.

*Length of stem.*—12-17cm.

*Diameter.*—0.6-0.8 cm.

*Length of internodes.*—1-2 cm.

*Texture.*—Glabrous.

*Color of peduncle.*—RHS 144B to RHS 144C.

*Length of peduncle.*—0.2-0.3 cm.

*Peduncle diameter.*—0.2 cm.

*Texture.*—Glabrous.

Inflorescence:

*Type.*—Terminal cyme with surrounding whorl of colored bracts.

*Flowering, botanically (opening of the stamen, shedding of pollen).*—Late November.

*Flowering, commercially (sufficiently colored bracts).*—Mid November.

*Flowering response time.*—About 7-7.5 weeks from equinox.

*Duration of flowering.*—Depends on light and environment, at least 4-6 weeks of 'shelf' life.

*Fragrance.*—Absent.

*Shape of inflorescence.*—Rosette-like whorl, star-shaped; bracts borne nearly horizontally to weakly funnel-shaped (slanting upright); tight center.

*Diameter of inflorescence.*—30 cm.

*Inflorescence, vertical diameter.*—5-8 cm.

*Number of completely colored bracts per inflorescence (sized over 2 cm).*—5-7.

*Single bract, shape.*—Ovate with relatively long, pointed tips, without or with weak lobes.

*Bract, apex.*—Acuminate.

*Bract, base.*—Weakly rounded.

*Single bract, length of blade.*—Up to 13.5 cm, younger bracts diminishing in size.

*Single bract, width of blade.*—7.5-11.5 cm.

*Bract color, upper side.*—Between RHS 51A and B.

*Bract color, lower side.*—RHS 51B and C.

*Vein color, upper surface.*—RHS 185A.

*Vein color, lower surface.*—Approximately RHS 51B.

*Texture.*—Weakly rugose, glabrous.

*Bract petiole color, upper surface.*—RHS 187B.

*Bract petiole color, lower surface.*—RHS 187C.

*Bract petiole, length.*—About 5.5 cm, shorter with younger bracts.

*Bract petiole diameter.*—0.2-0.3 cm.

Cyme (true inflorescence):

*Cyme, diameter.*—1.7-2.0 cm.

*Number of cyathia.*—5, borne in a tight cluster.

*Cyathium, shape.*—Ovate.

*Cyathium, diameter.*—0.2-0.5 cm.

*Cyathium, length.*—0.5-0.7 cm.

*Color.*—RHS 144A with RHS 146A spots, top is RHS 53B-C.

*Nectar cups.*—Usually one per cyathium.

*Nectur cup, width.*—0.3-0.5 cm.

*Nectar cup, color.*—RHS 144C.

Reproductive organs:

*Stamen (actually reduced male florets).*—Usually in a small bunch of 5-10 at the top of the cyathium.

*Shape.*—Strap-like.

*Filament length.*—0.2 cm.

*Filament color.*—RHS 53B-C.

*Anther color.*—RHS 46A.

*Anther diameter.*—0.1 cm.

*Pollen quantity.*—Moderate (normal quantity).

*Pollen color.*—RHS 12A.

*Female flowers.*—Not yet observed.

*Fertility/seed set.*—Has not been observed on this plant.

Disease/pest resistance: Disease/pest resistance has not been observed on this plant.

What is claimed is:

1. A new and distinct variety of Poinsettia plant named 'EURZ0003', substantially as illustrated and described herein.

* * * * *